(12) United States Patent
Rainey et al.

(10) Patent No.: US 11,823,446 B2
(45) Date of Patent: Nov. 21, 2023

(54) **METHOD OF USING GENETIC ARCHITECTURE OF PHENOMIC-ENABLED CANOPY COVERAGE IN *GLYCINE MAX***

(71) Applicant: Purdue Research Foundation, West Lafayette, IN (US)

(72) Inventors: Katherine Martin Rainey, West Lafayette, IN (US); Alencar Xavier, West Lafayette, IN (US); Keith Cherkauer, West Lafayette, IN (US); Anthony Hearst, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1392 days.

(21) Appl. No.: 15/894,427

(22) Filed: Feb. 12, 2018

(65) Prior Publication Data

US 2018/0232579 A1 Aug. 16, 2018

Related U.S. Application Data

(60) Provisional application No. 62/458,124, filed on Feb. 13, 2017.

(51) Int. Cl.
*G06V 20/10* (2022.01)
*A01H 1/04* (2006.01)
*G16B 20/00* (2019.01)

(52) U.S. Cl.
CPC ............ *G06V 20/188* (2022.01); *A01H 1/04* (2013.01); *G16B 20/00* (2019.02)

(58) Field of Classification Search
CPC ............ C12N 15/8261; C12N 15/8262; C12N 15/8267; Y02A 40/146; Y02A 40/10; A01H 1/04; A01H 3/00; A01H 1/00; A01H 1/045; A01H 1/12; A01H 1/121; A01H 6/542; A01H 1/021; A01H 5/12; G06V 20/188; G06V 20/17; G06V 20/13; G06V 20/10; G16B 20/00; G16B 20/40; G16B 45/00; G16B 50/20; G16B 50/30; G16B 40/00; G16B 25/00; G16B 30/00; G16B 20/20; G16B 30/10; G16B 5/00; G16B 50/00; C12Q 1/6895; C12Q 2600/13; C12Q 2600/156; C12Q 2600/172; A23L 11/03; A23L 11/07
See application file for complete search history.

(56) References Cited

U.S. PATENT DOCUMENTS 9,401,030 B2 * 7/2016 Nelan ................ G06T 7/90
11,334,986 B2 * 5/2022 Hearst ................ G06T 7/001
2018/0121726 A1 * 5/2018 Redden ............... A01G 22/00

OTHER PUBLICATIONS

Combined SoyBASE website and database pages, downloaded 2022, 36 pages. (Year: 2022).*
Bilyeu et al. EDS. Genetics, Genomics and Breeding of Soybean, 2010, CRC Press, Taylor and Francis Group, FL, 380 pages. (Year: 2010).*
Anderson, J. et al. A Roadmap for functional Structural Variants in the Soybean Genome (2014) G3, vol. 4 p1307 and supplemental info (Year: 2014).*
Campbell et al. Soybean (*Glycine max*) mutant and germplasm resources: current status and future prospects. (2016) Current Protocols in Plant Biology vol. 1 p. 307 (Year: 2016).*
Hao, D. et al. Identification of single nucleotide polymorphisms and haplotypes associated with yield and yield components in soybean (*Glycine max*) landraces across multiple environments. (2012) Theoretical applied genetics, vol. 124 pp. 447-458 and some supplemental information. (Year: 2012).*
Chapter 48, the GLM procedure. SAS Institute Inc. 2017. SAS/STAT® 14.3 User's Guide. Cary, NC: SAS Institute Inc. 196 pages. (Year: 2017).*
Yu, Chong. Improvement of soybean breeding via high throughput phenotyping and disease resistance. Dissertation, University of Illinois, Urbana (2016) 142 pages. (Year: 2016).*
Satopää et al. Combining multiple probability predictions using a simple logit model. (2014) International Journal of Forecasting vol. 30, pp. 344-356. (Year: 2014).*

* cited by examiner

*Primary Examiner* — Mary K Zeman
(74) *Attorney, Agent, or Firm* — Reichel Stohry Dean LLP; Natalie J. Dean (57) ABSTRACT

Digital imagery can help to quantify seasonal changes in desirable crop phenotypes that can be treated as quantitative traits. Because limitations in precise and functional phenotyping restrain genetic improvement in the post-genomic era, imagery-based phenomics could become the next breakthrough to accelerate genetic gains in field crops. Whereas many phenomic studies focus on exploratory analysis of spectral data without obvious interpretative value, we used field images to directly measure soybean canopy development from phenological stage V2 to R5. Over three years, we collected imagery using ground and aerial platforms of a large and diverse nested association panel comprising 5,555 lines. Genome-wide association analysis of canopy coverage across sampling dates detected a large quantitative trait locus on soybean (*Glycine max*, L. Merr.) chromosome 19. This QTL provided an increase in yield of 47.3 kg·ha$^{-1}$. Variance component analysis indicated that a parameter, described as average canopy coverage, is a highly heritable trait ($h^2$=0.77) with a promising genetic correlation with grain yield (0.87), enabling indirect selection of yield via canopy development parameters. Our findings indicate that fast canopy coverage is an early season trait that is inexpensive to measure and has great potential for application in breeding programs focused on yield improvement. We recommend using the average canopy coverage in multiple trait schemes, especially for the early stages of the breeding pipeline (including progeny rows and preliminary yield trials), in which the large number of field plots makes collection of grain yield data challenging.

17 Claims, 5 Drawing Sheets

METHOD OF USING GENETIC ARCHITECTURE OF PHENOMIC-ENABLED CANOPY COVERAGE IN GLYCINE MAX

CROSS REFERENCE

This application claims the benefit of U.S. Provisional Application 62/458,124 under 35 U.S.C. 119(e), filed on Feb. 13, 2017. The content of which is expressly incorporated herein entirely.

FIELD OF INVENTION

This disclosure is generally related to utilizing digital imagery techniques to predict plant phenotype. Particularly, direct measurement of soybean canopy development from various phenological stages and associating canopy development with genomic analysis provide indirect prediction on soybean phenotypes such as yield of biomass.

BACKGROUND

Information on spectral reflectance obtained from digital imagery can indicate a plant's chemical composition and physical properties. Imagery also provides useful information about plant architecture (1). Image data can produce multiple time series and spectral indices (2), for which limiting factors include the frequency with which pictures are taken during the growing season and the capabilities of the camera or sensor in a given wavelength spectrum (3). Recent phenomic studies employing imaging have focused on multi- and hyper-spectral capabilities (4, 5), with minimal investigation of time series of images for capturing crop development and canopy architecture (6). Yet plant architecture comprises a set of feature-driven traits that can contribute to genetic improvement of field crops. For instance, dwarfing (an architectural trait) is well-known for contributing to the yield increases attained from the Green Revolution (7, 8).

Imagery-based field phenotyping with high-throughput platforms has the potential to drive the discovery of novel traits and facilitate routine quantification of architectural, developmental, physiological, and phenological crop characteristics (9). Because it allows inexpensive evaluation of large numbers of field plots with multiple measures in a short period of time (2), such information provides an efficient framework to tackle phenotyping bottlenecks in plant breeding (5, 9, 10).

In contrast to point- or plant-based spectral reflectance, image analysis allows direct measurement of spatial or field-based traits that are known to be valuable, such as canopy coverage and vegetation indices, which are possible to collect from the field with high-throughput platforms, such as unmanned aircraft systems (UAS) (11, 12). Additionally, acquisition of imagery can be a robust approach, regardless of its collection platform, that is less sensitive to technical challenges and prevailing environmental conditions than other data acquisition methods. Thus, characterization and selection of phenotypes acquired from image analysis represents a low-hanging fruit for genetic improvement of yield potential in crops.

Increased crop yields often associate with greater biomass production (expressed as the product of total incident radiation throughout the duration of crop growth), the amount of light interception (LI) by crop canopies, and the conversion of chemical energy into plant dry matter (13). Improved LI from rapid canopy development is a significant contributor to increased biomass, total photosynthesis, and yield, which makes it an important target when selecting for genetically superior crops. Richards (2000) (13) proposed that genetic selection for improved LI has been occurring inadvertently since the beginning of crop domestication through the selection of young, competitive seedlings with fast crop growth rates, with this resulting in rapid canopy establishment and, therefore, greater LI during early vegetative growth. Many canopy parameters play dominant roles in determining source-sink ratios (14) along with light-use efficiency of the plant's photosynthetic machinery (15).

From 1924 to 2012, on-farm soybean yields increased approximately 23 kg·ha$^{-1}$ annually, due to both improved genetics and improved agronomic practices (16, 17, 18). Since the introduction of genomic tools in the past two decades, the rate of yield increase has grown to 66 kg·ha$^{-1}$ per year, where 50-66% of gain is associated with genetic improvement (19, 20). Recently, evaluation of soybean cultivars released between 1923 and 2007 determined that the greater biomass production and yield potential of newer cultivars is driven by linear increases in LI, efficiency of radiation use, and partitioning efficiency (21). At present, much of the existing genetic variation in photosynthetic efficiency and related processes is confined to undomesticated germplasm (22).

Purcell (2000) (23) developed a precise and rapid technique using ground-based digital imagery for evaluating seasonal variation in soybean canopy coverage. The methodology is based on the binary classification of individual pixels from plot images into canopy or background, thereby providing a direct quantification for the percent of canopy coverage on a continuous scale (23, 24). This research established a one-to-one relationship between fractional canopy coverage (determined through image analysis) and canopy light interception measurements acquired using a line quantum sensor, thereby facilitating the use of digital imagery to evaluate seasonal canopy interception of photosynthetically active radiation (PAR) (25, 26). While these findings greatly improved the efficiency with which we can assess LI, this method is impractical for use in large experiments that require phenotyping thousands of genetically distinct lines to determine gene-phenotype associations for complex traits (27).

Rapid canopy development in soybean optimizes growth dynamic parameters, providing a foundation for a greater biomass accumulation during the season and ultimately greater grain yield potential (28); it also favors early-season weed suppression (29, 30). Canopy coverage can be observed for the entire season, and it is likely that observed variation has a genetic basis and could be a target for genetic improvement. The objectives of this study were 1) to characterize imagery-based early-season canopy coverage in soybean as a trait with quantitative genetic control, 2) to describe the genetic architecture of canopy coverage via genome-wide association, and 3) to provide insight into the application of UAS quantification of canopy parameters for applications in soybean breeding aimed at improving yield.

Bridging Genomics and Phenomics

The application of marker-assisted selection (MAS) in plant breeding represented a critical step in selection practices driven by realized genetic information (31, 32). The applications of genomic tools evolved to whole-genome selection techniques, effective in selecting the favorable alleles in small-effect QTLs that govern low-heritability traits (33). However, poor phenotypic data quality is a major limitation for effective use of genomic prediction models (34, 35). More precise phenotypic information is necessary to accelerate the annual rate of genetic gain in field crops in the post-genomic era (36). Nevertheless, phenomic platforms can only be successful in crop improvement if they satisfy basic requirements that include high-throughput at a low cost (2, 37) and the ability to provide meaningful, heritable, and measurable trait information (11, 35).

SUMMARY

This study compellingly demonstrates the potential of unmanned aircraft systems (drones) to transform agricultural science through high-throughput phenotyping of valuable, previously intractable crop-growth parameters. Improved light interception significantly contributes to increased biomass, total photosynthesis, and yield in crop plants, which makes canopy development a breeding target to produce genetically superior crops. We used digital imagery to characterize early-season canopy development for three seasons in a soybean genetic mapping population and assessed its agronomic performance. We identified a strong genetic signal indicating the rate of canopy development and quantitative properties favorable for indirect selection for grain yield. We show how this robust, simple, and cost-effective phenotyping method can contribute to genetic improvement of crops, principally when yield potential estimates are inaccurate.

Data Availability: Phenotypes and genotypic data are available in the R package NAM. Load the data using the following command: data(met, package="NAM").

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Experiment Design

Our research used imagery acquired from ground and aerial platforms to characterize early-season canopy development for three years in a next-generation soybean genetic population, for which we also assessed agronomic performance. We developed methodology to automatically extract canopy data from the best quality aerial image of each plot, rather than using mosaics, quantifying the percentage of canopy pixels from over 70,000 ground images and over 2000 aerial images. Spatial statistics, a mixed model framework, and a logistic growth function served to calculate a parameter to describe multiple seasonally observed values of canopy coverage for each genetic line. Genomic data for the population helped determine the genetic architecture of the newly-described soybean trait. Examining the quantitative genetic properties then allowed us to propose the application of high-throughput field-based canopy phenotyping to increase the rate of genetic gain in soybean breeding pipelines.

Materials and Methods

Germplasm

The SoyNAM population is a nested association mapping panel consisting of around 5,600 F5-derived recombinant inbred lines (RILs) that originated as sets of 140 RILs descended from each of 40 bi-parental matings of 40 founder parents with one common, high yielding, hub parent (IA3023). The RILs exhibit maturities ranging from late MG II to early MG IV. The 40 founder parents include 17 cultivars or elite public breeding lines contributed by soybean breeders across the North Central Region, 15 unique breeding lines developed to have diverse ancestry, and 8 diverse plant introductions selected for their performance in water-limited environments. Visual canopy field images of the SoyNAM parents are available at the Soybase database created by the United States Department of Agriculture, which is publicly available. Genotyping of the lines employed an Illumina SoyNAM BeadChip SNP array designed for this population, using 5,305 single nucleotide polymorphism (SNP) markers identified from the genomic sequences of all 41 parental lines. We imputed missing SNP locus calls using random forest (38) and removed SNPs with a minor allele frequency smaller than 0.15 (39) using the R package NAM (38). This left a final total of 4,077 SNPs for the association analysis.

Field Design

In 2013, 2014, and 2015, we collected phenotypic data from the SoyNAM population in West Lafayette, Indiana. From 2012 to 2014, the experiment used a modified augmented design, and an augmented complete block design in 2015. Line planting took place on May 20, 2013; May 24, 2014; and May 23, 2015 at the Purdue University Agronomy Center for Research and Education (40°28'20.5"N 86°59'32.3"W). Experimental units were based on two-row plots (0.76 m×2.90 m) at a density of approximately 35 plants.m$^{-2}$. The 2012-2014 experiments grew all the SoyNAM entries, but the 2015 experiment grew only the six families (NAM5, NAM 9, NAM12, NAM15, NAM24, and NAM40) with the largest phenotypic variance for the traits of interest. The 2015 experiment experienced mild flood damage.

Canopy Coverage

Figure 1:
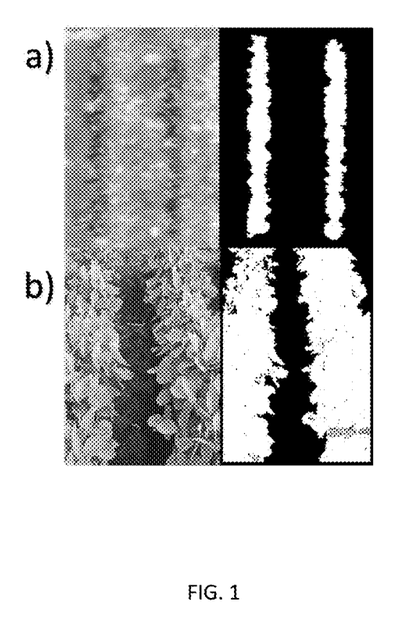
FIG. 1 Example canopy imagery of a single plot, used to calculate a percentage canopy coverage on a given sampling date. From aerial (above) or ground (below) platforms, with respective raw (left) and classified (right) imagery.

The metric we used to measure canopy coverage was the percentage of image pixels that were classified as canopy pixels (FIG. 1). We took images at regular intervals from two to eight weeks after planting, which spanned soybean phenological stages V2-R5 (40). The timeframe of data collection coincides with all but the final R5-R7 dry matter accumulation period (41). Collection of image data used ground-based (2013-2014) and aerial (2014-2015) platforms and images underwent a classification procedure to determine the number of pixels showing the soybean canopy.

Classification of ground-based images used SigmaScan Pro® software according to the methods of Karcher and Richardson (2005) (24). Appendix provides examples of classified ground imagery across the seasons. Classification of aerial images used a binomial model implemented in ENVI 5.0™ and calibrated with manually-labelled training data.

FIG. 1 Example canopy imagery of a single plot, used to calculate a percentage canopy coverage on a given sampling date. From aerial (above) or ground (below) platforms, with respective raw (left) and classified (right) imagery.

Using a logit link function for each field plot, we fit canopy coverage observations from multiple sampling dates into a logistic model, with the canopy coverage (cc) for any point in time (t) represented as $$cc_t = \frac{e^{(\beta_0+\beta_1 t)}}{1+e^{(\beta_0+\beta_1 t)}} \quad (1)$$

where $\beta_0$ and $\beta_1$ are the logistic regression coefficients for any given field plot. This function provided daily canopy coverage projections that were used to estimate canopy development parameters. The single-trait representation of canopy in this study is the average canopy coverage (ACC), defined as $$ACC = \int_{t_0}^{t_n} f(cc_t) \partial(cc_t) = \frac{1}{N}\sum_{t_0}^{t_n} cc_t \quad (2)$$

where N is the number of observed days, and $t_0$ and $t_n$ represent the first and last day of canopy coverage data collection. In essence, the ACC value is an arithmetical mean of multiple seasonally observed values of canopy coverage.

Ground-Based Imagery

Collection of images used to infer canopy coverage employed the methodology described by Purcell (2000) (23). We took Red-Green-Blue (RGB) pictures (680×480 pixels) at the center of each plot, about 1.5 m above the ground, at a 30° angle from the horizon, using a pocket camera (Canon PowerShot A400IS), then cropped these to 560×480 pixels to avoid capturing canopy from neighboring plots.

Aerial Imagery

In 2014, we collected aerial images using a Precision Hawk® unmanned aircraft system (UAS) equipped with a Nikon™ 1-J1 digital camera (3872×2592 pixels). It collected individual images at an altitude of 100 m, yielding a spatial resolution of 3.25 cm pixel$^{-1}$. In 2015, it collected images at 50 m using a Nikon™ 1-J3 digital camera (4608× 3072 pixels), yielding a spatial resolution of 1.50 cm pixel$^{-1}$. These images had a 70% lateral and forward overlap, which allowed image stitching using Pix4Dmapper™ software. Image stitching outputs, including estimated camera positions and orientations and plot map coordinates, helped to extract ortho-rectified image mosaics, digital surface models, camera positions and orientations for each aerial photo, and camera model parameters. These outputs were registered to map coordinates (easting, northing, and altitude) using ground control points. We obtained the map coordinates of the individual plots by gridding the image mosaics. The map coordinates of the plots, positions and orientations of the camera, camera model parameters, and a collinearity relationship were used to automatically identify which plots appeared in which images and extract ortho-rectified images of the plots directly from the aerial images (42).

Correspondence Between Platforms

Ganey and Block (1994) (43) reported that canopy coverage estimates from various methods are directly comparable. In 2014, we collected canopy data from both the ground and the UAS platforms and calculated ACC values for both platforms. A paired data set comparison provided evidence of suitably sufficient correspondence between the two platforms (FIG. 2), so we elected to collect data from the UAS platform only in 2015.

Figure 2:
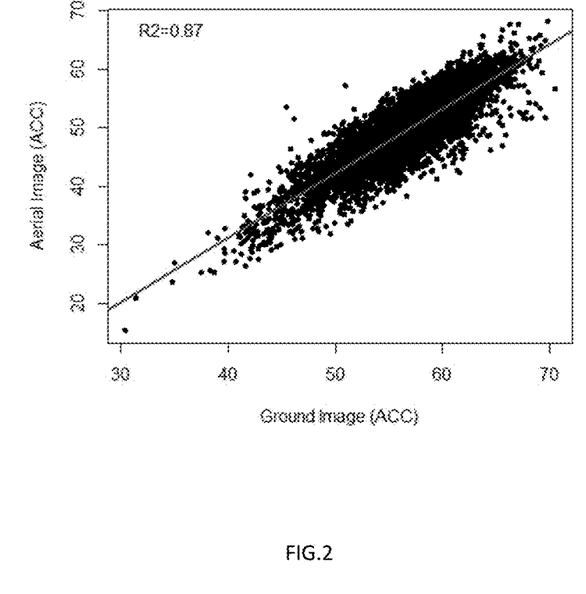
FIG. 2 Correspondence between the average canopy coverage measured from ground or aerial imagery from 2014.

FIG. 2 Correspondence between the average canopy coverage measured from ground or aerial imagery from 2014.

Statistical Model

Correlation and genome-wide association analysis used genetic values obtained from best linear unbiased prediction estimators, rather than observed phenotypes of canopy coverage from individual time points. The following mixed linear model was used to provide the genetic values $$y = 1\mu + f(x) + Zu + Wg + e \quad (3)$$

where y is the vector of observed phenotypes, $\mu$ is the intercept, f(x) is the function that accounts for the spatial heterogeneity of field variation as the average phenotypic value of neighbor plots (44), Z is the incidence matrix of environment, u is the vector of regression coefficients for the environment, W is the incidence matrix of genotypes, g is the vector of genetic values, and e is the vector of residuals. Genotypes were treated as random effects, assumed to be normally and independently distributed as g~N(0, I$\sigma_g^2$). Likewise, residuals were assumed to be normally and independently distributed as e~N(0, I$\sigma_e^2$).

Association Analysis

Genome-wide association analysis used the random effect model designed for next-generation populations (45), implemented in the R package NAM (38), for individual canopy coverage measurement days spanning 14 to 56 days after planting, using a random linear effect model:

$$g = 1\mu + X\alpha + \psi + \varepsilon \quad (4)$$

where g is the vector of genetic values of canopy coverage for a given point in time as described in equation (3), $\mu$ is the intercept, X is the incidence matrix of haplotypes generated from marker data, $\alpha$ is the vector of regression coefficients, $\psi$ corresponds to the polygenic coefficients, and $\varepsilon$ is the vector of residuals. Random effect coefficients were assumed to be normal as $\alpha$~N(0, I$\sigma_\alpha^2$), $\psi$~N(0, K$\sigma_\psi^2$) and $\varepsilon$~N(0, I$\sigma_e^2$), where K represents the genomic relationship matrix.

We evaluated statistical significance using a likelihood ratio test by comparing the log-likelihood of the model with the marker included ($L_1$) to the reduced model ($L_0$) not including the marker. Thus, $$LRT = -2(L_1 - L_0). \quad (5)$$

In the random model, the LRT follows a mixture of chi-squared and binomial distributions (38) with p-values computed using a chi-squared distribution with 0.5 degrees of freedom. The Bonferroni threshold that accounts for false positives under multiple hypothesis testing (α=0.05) was used to define which markers were associated with the trait of interest. The expected threshold for 4,077 SNPs markers was estimated 4.91−log (p-value).

Phenotyping of Agronomic Traits

Grain yield was measured as grams of seed per plot, converted to kg·ha$^{-1}$ using harvest-timed seed moisture to adjust all plot values to 13% seed moisture. We collected maturity data twice a week as the number days after planting (DAP), back and forward scoring plots that flowered and matured between the intervals. The criterion for a plot to achieve maturity (R8) was 50% of the plants having 95% of their pods mature (40).

Variance Component Analysis

We computed Pearson and Spearman correlations from the phenotypic data using built-in R functions. A multivariate mixed linear model, based on equation (3) estimated covariance components for each of the three traits: grain yield, days to maturity, and average canopy coverage. Model fitting used the AI-REML algorithm (46) implemented in AIREMLF90 (47) with the covariance structure set up as follows:

$$\text{Var}(Y) = (G \otimes \Sigma_g + I \otimes \Sigma_e) \quad (6)$$

Here G represents the realized genomic relationship matrix. Matrices $\Sigma_g$ and $\Sigma_e$ represent the genetic and residual covariance matrices among the three traits. These covariance components then helped to estimate the heritability of average canopy coverage, grain yield, and days to maturity, as well as the genetic correlations among these traits.

Results and Discussion

Canopy Behavior

Figure 3:
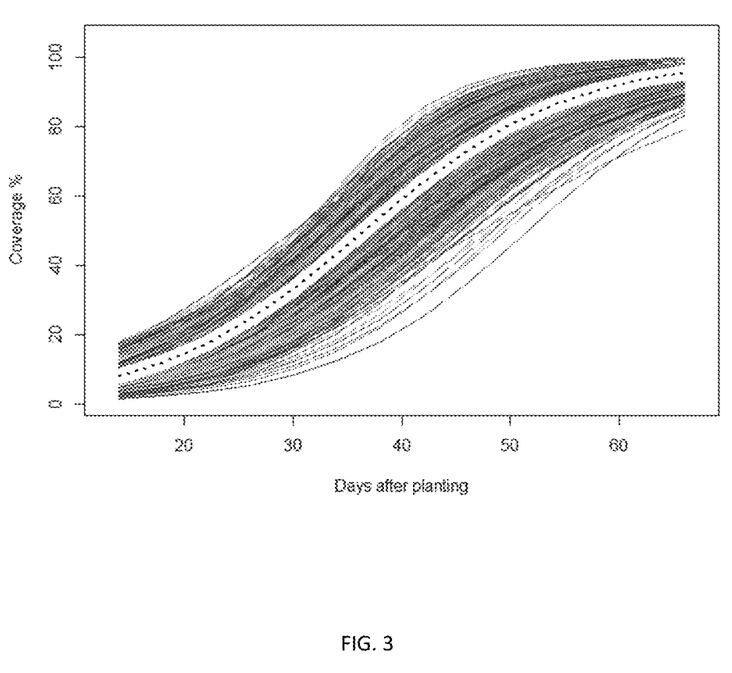
FIG. 3 Development of canopy coverage in the SoyNAM population described as logistic curves of canopy development for individual soybean lines over two or three seasons. Each curve describes an individual soybean line. The white dotted curve represents the mean curve.

Individual lines showed the potential to attain full canopy coverage (100%) as early as 50 DAP, while others did not reach full coverage within 64 DAP (FIG. 3). In the latter case, lines seemed incapable of closing the canopy entirely in a production system employing a row spacing of 76 cm. Reports indicate that yield and canopy traits are under similar genetic control when grown using narrower row spacing, with slight changes in heritability (48, 49).

FIG. 3 Development of canopy coverage in the SoyNAM population described as logistic curves of canopy development for individual soybean lines over two or three seasons. Each curve describes an individual soybean line. The white dotted curve represents the mean curve.

Genome-Wide Association

Figure 4:
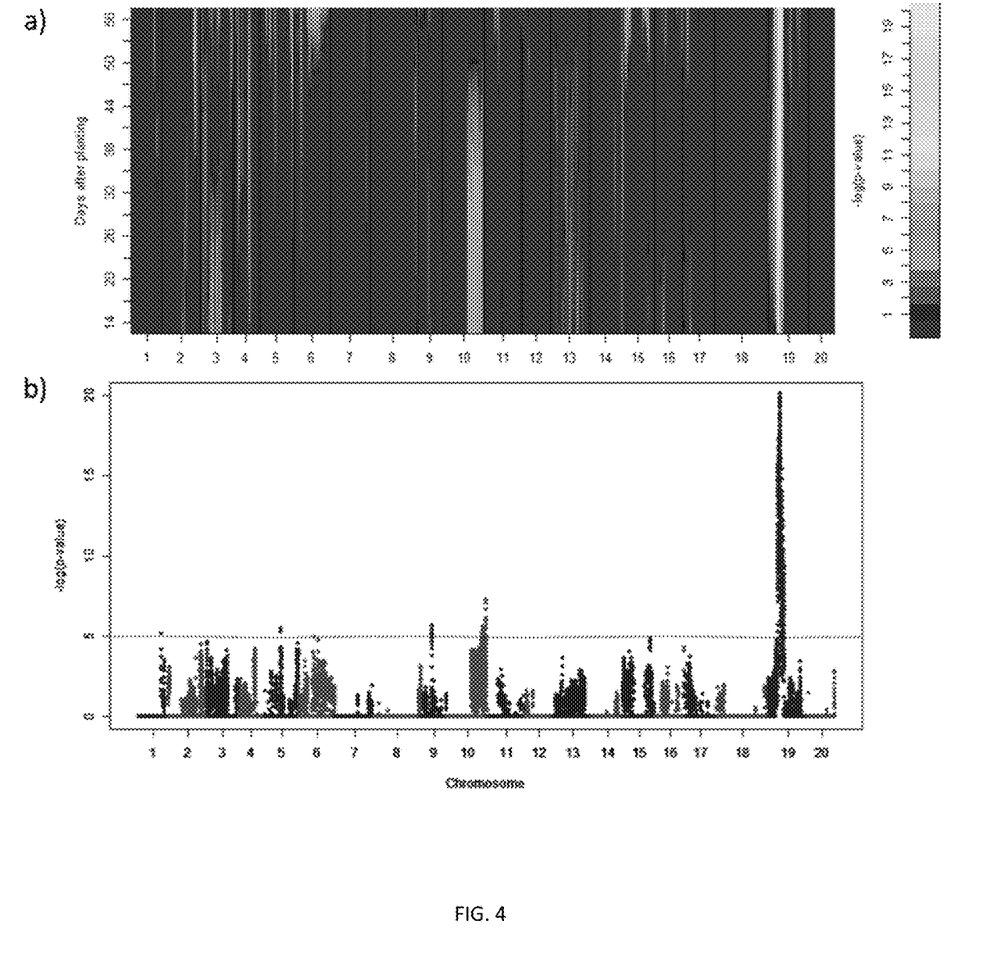
FIG. 4 Results of the genome-wide association study for canopy coverage. Genomic regions significantly associated with early-season soybean canopy coverage for two or three years observed or estimated for a) each day from 14 to 56 days after planting, and b) across all days.

Six genomic regions, on soybean chromosomes 1, 5, 6, 9, 10, and 19, associated with canopy coverage when measured or estimated across all days (FIG. 4b). The largest effect QTL detected was on chromosome 19, and it associated with canopy coverage on all days within the survey period (FIG. 4a). The second largest effect QTL was located on chromosome 10, and was significant for approximately two-thirds of the survey period, from 14 to 26 DAP. Table 1 summarizes the QTLs detected, the period during which these QTLs were significant, and their average allelic effects on ACC, grain yield, and maturity.

FIG. 4 Results of the genome-wide association study for canopy coverage. Genomic regions significantly associated with early-season soybean canopy coverage for two or three years observed or estimated for a) each day from 14 to 56 days after planting, and b) across all days.

The existence of large-effect QTLs along with several nearly-significant associations indicate that ACC is controlled by major genes in the soybean genome. Another canopy trait, early-season canopy height, was reported to be heritable (h$^2$=0.64) and genetically correlated to weed-suppression ability ($\rho_{x,y}$=0.80) (50).

The genome-wide association presented by day (FIG. 4a) shows that the chromosome 19 QTL was significant throughout the survey period. Other associations were significant either earlier or later in the season, or when the canopy was nearly closed (Table 1). Thus, early- and late-season canopy growth are controlled through independent genetic mechanisms and can be dissected into distinct traits. This agrees with Jannink et al. (2001) (51) who, studying the genetic basis of competition, also observed the independence of genetic control between early- and late-season canopy development in soybeans.

TABLE 1

Single nucleotide polymorphisms (SNP) significantly associated with early-season soybean canopy coverage and the number of days after planting (DAP) during which they were significant. Mean change in phenotypic values associated with each QTL in terms of grain yield (GY) expressed as kilograms per hectare, number of DAP to maturity (R8), and the percentage of average canopy coverage (ACC), calculated as the allelic substitution of the homozygous founder parent genotype for the homozygous IA3023 genotype.

| SNP | Period of Significant Association (DAP) | GY (kg · ha$^{-1}$) | R8 (DAP) | ACC (%) |
| --- | --- | --- | --- | --- |
| Gm01_50911939_C_T | 56 | −26.04 | −1.12 | −0.36 |
| Gm05_37467797_A_G | 53-56 | −44.71 | 0.08 | −0.65 |
| Gm06_14104090_T_C | 56 | 99.58 | 0.50 | 0.55 |
| Gm09_4034850_C_T | 14-35, 59-64 | 12.24 | −0.60 | −0.44 |
| Gm010_44120764_T_C | 14-23 | 5.95 | −0.59 | 0.04 |
| Gm010_44630777_C_A | 14-26 | 51.61 | 1.06 | 0.33 |
| Gm019_1586092_T_C | 14-64 | 47.30 | −0.24 | 1.34 |

Assuming pleiotropy, the estimated increase in grain yield associated with the positive allele of the chromosome 19 QTL was 47.30 kg·ha$^{-1}$. Importantly, this increase did not also increase days to maturity (−0.24 days).

Quantitative Genetic Properties of Average Canopy Closure

Variance components provide an insight about the level of genetic and environmental control of the traits of interest, necessary to estimate heritability (Table 2). At multivariate level, (co)variances indicate the nature of the relationship between multiple traits, uncovering whether traits are more associated at genetic or environmental level (Table 3).

TABLE 2

Variance components of the traits considered in this study. Genetic (G) and environmental (E) variances and heritabilities for soybean grain yield (GY), and days to maturity (R8), and average canopy coverage (ACC).

|  | GY | R8 | ACC |
| --- | --- | --- | --- |
| Var(G) | 78.80 | 208.36 | 25.54 |
| Var(E) | 56.12 | 9.39 | 8.10 |
| h$^2$ | 0.58 | 0.96 | 0.76 |

For ACC to be an effective predictor of grain yield potential in the early stages of breeding pipelines, the phenotypic correlations, and more importantly the genetic correlations, must be high between the two traits. The genetic correlation between grain yield and ACC is quite high (Table 3), but so are the correlations between days to maturity and ACC and between grain yield and days to maturity. However, as noted above, the main allelic effect of the chromosome 19 QTL affects ACC and yield, without negatively impacting days to maturity.

TABLE 3

Phenotypic (P), Spearman (S), genetic (G), and environmental (E) correlations among grain yield (GY), average canopy coverage (ACC) and days to maturity (R8).

|  | GY-ACC | R8-ACC | GY-R8 |
|---|---|---|---|
| Cor(P) | 0.63 | 0.31 | 0.42 |
| Cor(S) | 0.70 | 0.38 | 0.46 |
| Cor(G) | 0.88 | 0.77 | 0.72 |
| Cor(E) | 0.18 | −0.06 | 0.23 |

Selection for Canopy Coverage

A faster rate of canopy coverage development (achieved through manipulation of crop management practices) increases light interception, suppresses weeds, and has other beneficial properties (23, 51, 52, 53). As a target for artificial selection, the trait presents attractive genetic properties, such as high heritability and strong genetic correlation with grain yield that allows for indirect selection or prediction of grain yield potential.

For indirect selection to be effective, the response of grain yield potential when selecting for ACC must be greater than the response of selecting for yield directly. Very few cases of successful indirect selection have been reported (54). The indirect selection equation indicates that efficient indirect selection for yield at the same selection intensity is possible with ACC because the correlated response (CR) to selection for grain yield is 14% greater than the direct response (R):

$$\rho_{cc,y} = \frac{CR}{R} = \frac{h_{cc}^2 \times r_{cc,y}}{h_y^2} = \frac{0.76 \times 0.88}{0.58} = 1.14. \quad (7)$$

In the equation above, $h_{cc}^2$ represents the heritability of the secondary trait (i.e. ACC), $r_{cc,y}$ is the genetic correlation between primary and secondary traits, and $h_y^2$ is the heritability of the primary trait (i.e. grain yield potential). Thus, assuming identical selection intensities, indirect selection of grain yield using average canopy coverage would be expected to be better than direct selection for yield. Although the canopy traits reported by Jannink et al. (2001) (51) did not show maturity-mediated tradeoffs, use of selection indices including both ACC and days to maturity may be necessary to mitigate indirect increases in maturity.

Genetic and phenotypic variation in soybean canopy coverage exists because it is a novel and unexploited trait with little history of artificial selection. The SoyNAM population used here is a diverse genetic panel subject to minimal selection, whereas commercial germplasm would likely exhibit less phenotypic variance. In that case, the calculated correlated response and overall trait heritabilities may not be as favorable.

Our results support the use of average canopy coverage to predict lines with high grain-yield potential when collection of accurate yield data is not feasible or is challenging. This is often the case during early generations in a breeding pipeline when yield data are of low quality due to low seed number, or when limited resources are available for the evaluation of many lines, as in preliminary yield trials. ACC may also be useful in selection indices that include grain yield and other valuable traits.

UAS Phenotyping and Phenomics

From the perspective of genetic improvement of crops, traits with known properties that can be collected in situ using UAS platforms are a low-hanging fruit, in particular canopy characteristics and vegetation indices (11, 12). In addition to being robust, simple, and cost-effective, these traits are likely more valuable than measurements made in controlled environments for physiological characteristics that cannot be translated into field phenotypes and which seldom provide economic advantages (2, 55). Here we have shown canopy coverage to be a highly heritable trait associated with grain yield potential, possibly the most promising phenomic trait reported thus far.

Accounting for Environmental Noise

This study used spatial statistics in its model, which provided a covariate term that accounted for micro-environmental field variation, or environmental noise, on a plot-by-plot basis (44). Without this adjustment, the heritability of ACC was estimated to be 0.46 (not shown), though the magnitude of the genetic correlation of ACC with grain yield remained the same. Previous studies (56, 57) described the importance of considering spatial structure among field observations to achieve proper estimation of statistically-estimated trait values, or breeding values. Many authors report the challenge of differentiating between signal and noise in phenomic data collected from the field (9, 35, 37). We conclude that analysis of field phenomic traits should not ignore spatial information (i.e. kriging).

Breeding Values Incorporating Phenomic Data

Research is beginning to explore the optimal application of phenomic traits in genetic improvement of crop plants, and how selection schemes and prediction models should accommodate phenomic information. Phenomic quantifications from field imagery are indicators of plant health and development (12), but inclusion of such measurements as covariates in genomic models can be controversial (58) because they share both a genetic and an environmental correlation with agronomic traits (Tab. 3). Instead, phenomic traits might be more suitably used in multi-trait models, to improve the accuracy of estimated breeding values by exploiting genetic correlations and, therefore, preserve the genetic nature of the association between the target trait and phenomic trait. We showed that canopy coverage displays a high correlation with valuable soybean traits (Table 3), that favors multivariate models and enhances the accuracy of breeding values.

Figure 5:
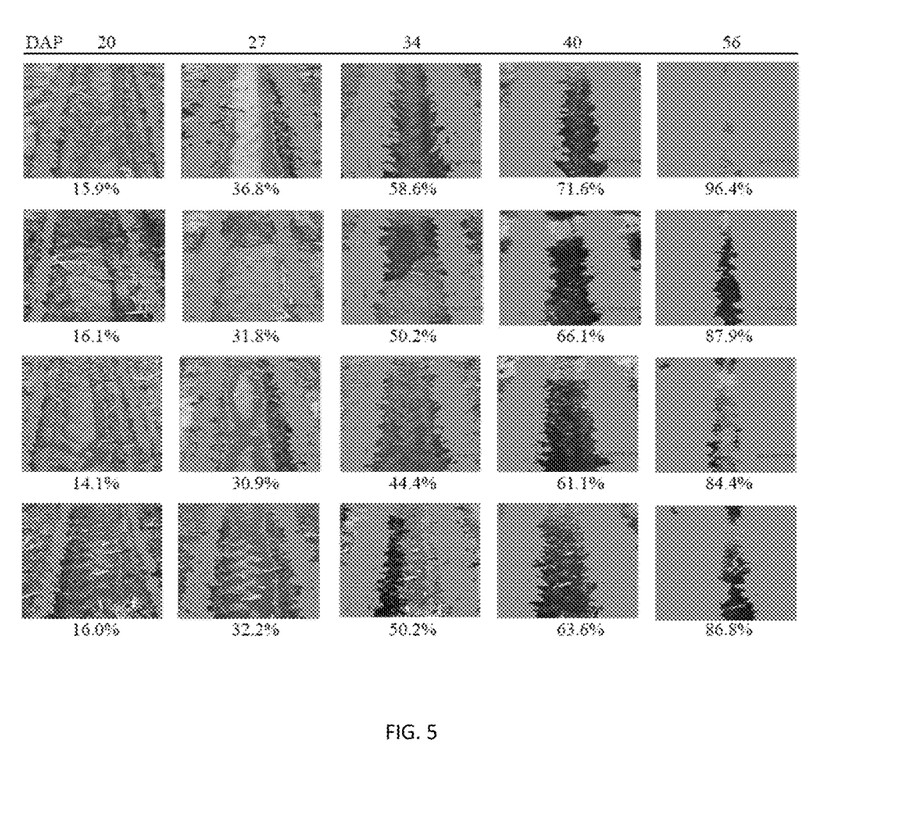
FIG. 5 Time series of seasonal canopy coverage during the 2014 growing season. Each row represents classified images for a day after planting (DAP) for four randomly selected plots. Values below each image represent the percentage canopy coverage derived through image classification from left, ground images, and, right, aerial images.

FIG. 5. Time series of seasonal canopy coverage during the 2014 growing season. Each row represents classified images for a day after planting (DAP) for four randomly selected plots. Values below each image represent the percentage canopy coverage derived through image classification from left, ground images, and, right, aerial images.

REFERENCES

1. Yol E, Toker C, & Uzun B (2015). Traits for Phenotyping. *Phenomics in Crop Plants: Trends, Options and Limitations* eds. Kumar J, Pratap A, Kumar S (Springer, India), pp. 11-26.
2. White J W, Andrade-Sanchez P, Gore M A, Bronson K F, Coffelt T A, Conley M M, . . . & Jenks M A (2012). Field-based phenomics for plant genetics research. *Field Crops Research*, 133: 101-112.
3. Andrade-Sanchez P, Gore M A, Heun J T, Thorp K R, Carmo-Silva A E, French A N, . . . & White J W (2014)

Development and evaluation of a field-based high-throughput phenotyping platform. *Functional Plant Biology*, 41(1): 68-79.
4. Yang W, Duan L, Chen G, Xiong L, & Liu Q (2013) Plant phenomics and high-throughput phenotyping: accelerating rice functional genomics using multidisciplinary technologies. *Current Opinion in Plant Biology*, 16(2): 180-187.
5. Kumar J, Pratap A, & Kumar S (2015) Plant Phenomics: An Overview. *Phenomics in Crop Plants: Trends, Options and Limitations* eds. Kumar J, Pratap A, Kumar S (Springer, India), pp. 1-10.
6. Schunk C R, Eberius M, Shu Q Y, Forster B P, & Nakagawa H (2012) Phenomics in plant biological research and mutation breeding. *Plant Mutation Breeding and Biotechnology*: 535-560.
7. Hammer G L, Dong Z, McLean G, Doherty A, Messina C, Schussler J, . . . & Cooper M (2009) Can changes in canopy and/or root system architecture explain historical maize yield trends in the US corn belt? *Crop Science*, 49(1): 299-312.
8. Swaminathan M S (2014) Norman Borlaug and a hunger-free world. *Resonance*, 19(2): 109-115.
9. Araus J L, & Cairns J E (2014) Field high-throughput phenotyping: the new crop breeding frontier. *Trends in Plant Science*, 19(1): 52-61.
10. Furbank R T, & Tester M (2011) Phenomics-technologies to relieve the phenotyping bottleneck. *Trends in plant science*, 16(12): 635-644.
11. Cabrera-Bosquet L, Crossa J, von Zitzewitz J, Serret M D, & Luis Araus J (2012) High-throughput Phenotyping and Genomic Selection: The Frontiers of Crop Breeding Converge. *Journal of Integrative Plant Biology*, 54(5): 312-320.
12. Liebisch F, Kirchgessner N, Schneider D, Walter A, & Hund A (2015) Remote, aerial phenotyping of maize traits with a mobile multi-sensor approach. *Plant Methods*, 11(1): 1.
13. Richards, R A (2000) Selectable traits to increase crop photosynthesis and yield of grain crops. Journal of Experimental Botany, 51: 447-458.
14. Board J E, & Harville B G (1993) Soybean yield component responses to a light interception gradient during the reproductive period. *Crop Science*, 33(4): 772-777.
15. Tharakan P J, Volk T A, Nowak C A, & Ofezu G J (2008) Assessment of canopy structure, light interception, and light-use efficiency of first year regrowth of shrub willow (*Salix* sp.). *BioEnergy Research*, 1(3-4): 229-238.
16. Rincker K Nelson R, Specht J, Sleper D, Cary T, Cianzio S R, & Diers B (2014) Genetic improvement of US soybean in maturity groups II, III, and IV. *Crop Science* 54(4): 1419-1432.
17. Specht J E, Diers B D, Nelson R L, de Toledo J F F, Torrion J A, and Grassini P (2014) Soybean (*Glycine max* (L.) Merr.) *Yield Gains in Major US Field Crops CSSA Special Publication* 33 eds. Smith S, Diers B. Specht J, and Carver B. American Society of Agronomy, Crop Science Society of America, Soil Science Society of America. Madison, WI.
18. Suhre J J, Weidenbenner N H, Rowntree S C, Wilson E W, Naeve S L, Conley S P, . . . & Davis V M (2014) Soybean yield partitioning changes revealed by genetic gain and seeding rate interactions. *Agronomy Journal*, 106(5): 1631-1642.
19. Board J E, & Kahlon C S (2011) *Soybean yield formation: what controls it and how it can be improved.* INTECH Open Access Publisher.
20. Rowntree S C, Suhre J J, Weidenbenner N H, Wilson E W, Davis V M, Naeve S L, . . . & Conley S P (2013) Genetic gain×management interactions in soybean: I. Planting date. *Crop Science*, 53(3): 1128-1138.
21. Koester R P, Skoneczka J A, Cary T R, Diers B W, & Ainsworth E A (2014) Historical gains in soybean (*Glycine max* Merr.) seed yield are driven by linear increases in light interception, energy conversion, and partitioning efficiencies. *Journal of Experimental Botany*, 65(12): 3311-3321.
22. Sherman-Broyles S, Bombarely A, Powell A F, Doyle J L, Egan A N, Coate J E, & Doyle J J (2014) The wild side of a major crop: Soybean's perennial cousins from Down Under. *American Journal of Botany*, 101(10): 1651-1665.
23. Purcell L C (2000) Soybean canopy coverage and light interception measurements using digital imagery. *Crop Science* 40(3): 834-837.
24. Karcher D E, & Richardson M D (2005) Batch analysis of digital images to evaluate turfgrass characteristics. *Crop Science*, 45(4): 1536-1539.
25. Purcell L C, Ball R A, Reaper J D, & Vories E D (2002) Radiation use efficiency and biomass production in soybean at different plant population densities. Crop Science, 42(1): 172-177.
26. Edwards J T, Purcell L C, & Karcher D E (2005) Soybean yield and biomass responses to increasing plant population among diverse maturity groups: II, Light interception and utilization. Crop Science, 45(5):1770-1777.
27. Myles, S, Peiffer, J, Brown, P J, Ersoz, E S, Zhang, Z, Costich, D E, & Buckler, E S (2009) Association mapping: Critical considerations shift from genotyping to experimental design. The Plant Cell, 21(8): 2194-2202.
28. Hall B (2015) *Quantitative characterization of canopy coverage in the genetically diverse SoyNAM population* (Master's dissertation). Purdue University.
29. Jannink J L, Lorenz A J, and Iwata H (2010) Genomic selection in plant breeding: from theory to practice. Briefings in Functional Genomics, 9(2):166-177.
30. Fickett N D, Boerboom C M, & Stoltenberg D E (2013) Soybean yield loss potential associated with early-season weed competition across 64 site-years. *Weed Science*, 61(3): 500-507.
31. Muir W M (2007) Comparison of genomic and traditional BLUP-estimated breeding value accuracy and selection response under alternative trait and genomic parameters. *Journal of Animal Breeding and Genetics* 124(6): 342-355.
32. Hayes B J, Visscher P M, & Goddard M E (2009) Increased accuracy of artificial selection by using the realized relationship matrix. *Genetics Research*, 91(01): 47-60.
33. Heffner E L, Sorrells E, & Jannink J L (2009) Genomic selection for crop improvement. *Crop Science*, 49(1): 1-12.
34. de los Campos G, Hickey J M, Pong-Wong R, Daetwyler H D, & Calus M P (2013) Whole-genome regression and prediction methods applied to plant and animal breeding. *Genetics*, 193(2): 327-345.
35. Cobb J N, DeClerck G, Greenberg A, Clark R, & McCouch S (2013) Next-generation phenotyping: requirements and strategies for enhancing our understanding of genotype-phenotype relationships and its relevance to crop improvement. *Theoretical and Applied Genetics*, 126(4): 867-887.

36. Henryon M, Berg P, & Sørensen A C (2014) Animal-breeding schemes using genomic information need breeding plans designed to maximise long-term genetic gains. *Livestock Science*, 166: 38-47.
37. Basu P S, Srivastava M, Singh P, Porwal P, Kant R, & Singh J (2015) High-Precision Phenotyping Under Controlled Versus Natural Environments. *Phenomics in Crop Plants: Trends, Options and Limitations* eds. Kumar J, Pratap A, Kumar S (Springer, India). pp. 27-40
38. Xavier A, Xu S, Muir W M, & Rainey K M (2015) NAM: association studies in multiple populations. *Bioinformatics*. 31(23): 3862-3864.
39. Xavier A, Muir W M, & Rainey K M (2016). Assessing predictive properties of genome-wide selection in soybeans. *G3: Genes|Genomes|Genetics*, 6(8), 2611-2616.
40. Fehr W R, Caviness C E, Burmood D T, & Pennington J S (1971) Stage of development descriptions for soybeans, *Glycine max* (L.) Merrill. *Crop Science*, 11(6): 929-931.
41. Egli D B, & Leggett J E (1973) Dry matter accumulation patterns in determinate and indeterminate soybeans. *Crop Science*, 13(2): 220-222.
42. Kasser, M (2002). *Digital Photogrammetry*. London; New York: London; New York: Taylor & Francis.
43. Ganey J L, & Block W M (1994) A comparison of two techniques for measuring canopy closure. *Western Journal of Applied Forestry*, 9(1): 21-23.
44. Lado B, Matus I, Rodríguez A, Inostroza L, Poland J, Belzile F, . . . & von Zitzewitz J (2013) Increased genomic prediction accuracy in wheat breeding through spatial adjustment of field trial data. *G3: Genes|Genomes|Genetics*, 3(12): 2105-2114.
45. Wei J. & Xu S (2015) A Random Model Approach to QTL Mapping in Multi-parent Advanced Generation Inter-cross (MAGIC) Populations. *Genetics*, 2(202): 471-486.
46. Gilmour A R, Thompson R, & Cullis B R (1995) Average information REML: an efficient algorithm for variance parameter estimation in linear mixed models. *Biometrics*, 1440-1450.
47. Misztal I, Tsuruta S, Strabel T, Auvray B, Druet T, & Lee D H (2002, August) *BLUPF90 and related programs (BGF90)* Proceedings of the 7th world congress on genetics applied to livestock production (Vol. 28, pp. 21-22). Montpellier, Communication No. 28-27.
48. Weaver D B, & Wilcox J R (1982) Heritabilities, gains from selection, and genetic correlations for characteristics of soybeans grown in two row spacings. *Crop Science*, 22(3): 625-629.
49. De Bruin J L, & Pedersen P (2008) Effect of row spacing and seeding rate on soybean yield. *Agronomy Journal*, 100(3): 704-710.
50. Jannink J L, Orf J H, Jordan N R, & Shaw R G (2000). Index selection for weed suppressive ability in soybean. *Crop Science*, 40(4): 1087-1094.
51. Jannink J L, Jordan N R, & Orf J H (2001) Feasibility of selection for high weed suppressive ability in soybean: Absence of tradeoffs between rapid initial growth and sustained later growth. *Euphytica*, 120(2): 291-300.
52. Martius C, Höfer H, Garcia M V, Römbke J, Förster B, & Hanagarth W (2004) Microclimate in agroforestry systems in central Amazonia: does canopy closure matter to soil organisms? *Agroforestry Systems*, 60(3): 291-304.
53. Campillo C, Prieto M H, Daza C, Monino M J, & Garcia M I (2008) Using digital images to characterize canopy coverage and light interception in a processing tomato crop. *Hortscience*, 43(6): 1780-1786.
54. Bernardo R (2010) *Breeding for Quantitative Traits in Plants*. Stemma Press.
55. Von Mogel K H (2013) Taking the phenomics revolution into the field. *CSA News*, March: 4-10
56. Piepho H P, Möhring J, Melchinger A E, & Büchse A (2008) BLUP for phenotypic selection in plant breeding and variety testing. *Euphytica*, 161(1-2): 209-228.
57. Oakey H, Cullis B, Thompson R, Comadran J, Halpin C & Waugh R. (2016). Genomic Selection in Multi-environment Crop Trials. *G3: Genes|Genomes|Genetics*, 6(5), 1313-1326.
58. Valente B D, Morota G, Peñagaricano F, Gianola D, Weigel K, & Rosa G J (2015) The causal meaning of genomic predictors and how it affects construction and comparison of genome-enabled selection models. *Genetics*, 200(2): 483-494.

The invention claimed is:

1. A method for selection of one or more breeder lines with a desired phenotype in *Glycine max* soybean plants, the method comprising:
   measuring canopy coverage development at regular intervals in a one or more planted populations of *Glycine max* soybean germplasm for a period of time comprising a number of observed;
   calculating an average canopy coverage (ACC) for each of the one or more planted populations of *Glycine max* soybean germplasm using equation (2):

$$ACC = \int_{t_0}^{t_n} f(cc_t) \partial(cc_t) = \frac{1}{N} \sum_{t_0}^{t_n} cc_t \tag{2}$$

wherein N is the number of observed days, cc is the canopy coverage for any point in time (t) within the time period for each population, $t_0$ is a first day of the time period, and $t_n$ is a last day of the time period;
   comparing the calculated ACC of each of the one or more planted populations with a reference ACC, the reference ACC calculated using equation (2) and canopy coverage measurements taken over the period of time from a reference population of *Glycine max* soybean germplasm with a desired phenotype, wherein a calculated ACC from the one or more planted populations matching or being higher than the reference ACC is indicative of such population of *Glycine max* soybean germplasm exhibiting the desired phenotype;
   selecting the one or more planted populations of *Glycine max* soybean germplasm as a breeder line where the calculated ACC of such population matches or is higher than the reference ACC; and
   planting and growing a progeny crop descendant from the selected breeder line that expresses the desired phenotype;
   wherein the desired phenotype is grain yield in under 56 days after planting (DAP) and associated with at least one quantitative trait locus at soybean chromosomes 1, 5, 6, 9, 10, or 19 and selected from the group consisting of Gm06_14104090_T_C; Gm09_4034850_C_T, Gm010_44120764_T_C, and Gm019_1586092_T_C.

2. The method according to claim 1, wherein measuring the canopy coverage development comprises taking aerial images of the one or more planted populations of *Glycine max* soybean germplasm at regular intervals over the period of time.

3. The method according to claim 1, wherein the primary genetic trait is biomass production.

4. The method according to claim 1, wherein the canopy coverage measurements of the reference population are collected by high throughput screening of the reference population of *Glycine max* soybean germplasm with the desired phenotype.

5. The method according to claim 1, wherein the canopy coverage development is measured by drone pictures.

6. The method according to claim 1, wherein the one or more planted populations of *Glycine max* soybean germplasm is a SoyNAM population.

7. The method of claim 1, further comprising:
storing a model to predict potential crop yield in a reference population of *Glycine max* soybean germplasm on a computer system, the model comprising digitally generated data used to compute potential crop yield as a function of the reference ACC and a genetic trait correlated with the desired phenotype.

8. The method of claim 1, further comprising the step of:
receiving unprocessed and digitally generated data, wherein the data comprises a plurality of values used to compute potential crop yield as a function of the calculated ACC of the one or more populations of *Glycine max* soybean germplasm and a genetic trait correlated with the desired phenotype.

9. The method of claim 1 further comprising the step of:
extracting a number of pixels that contribute to a canopy cover for the one or more planted populations of *Glycine max* soybean germplasm from a plurality of ground and aerial images taken of the one or more planted populations at regular intervals over the period of time.

10. The method of claim 1 further comprising the step of:
computing a percent canopy coverage for the one or more planted populations of *Glycine max* soybean germplasm using a logit link function for each of a plurality of timepoints within the period of time.

11. The method of claim 1 further comprising the step of:
computing an arithmetical mean of multiple seasonally observed values of canopy coverage to provide the calculated ACC of the one or more planted populations of *Glycine max* soybean germplasm.

12. The method of claim 1 further comprising the step of:
identifying one or more quantitative trait loci using a random linear effect model as a function of the calculated ACC of the one or more planted populations of *Glycine max* soybean germplasm and a plurality of genetic marker data calculated from the one or more planted populations of *Glycine max* soybean germplasm.

13. The method of claim 1 further comprising the step of:
creating a realized genomic relationship matrix to estimate one or more of the indices selected from the group consisting of heritability, days to maturity, and genetic correlation.

14. The method of claim 2, further comprising the step of:
processing raw data from the aerial images to produce an ortho-rectified image.

15. The method of claim 1, wherein the period of time comprises two to eight weeks after planting the one or more planted populations of *Glycine max* soybean germplasm.

16. A method for selection of one or more breeder lines with a desired phenotype in *Glycine max* soybean plants, the method comprising:
measuring canopy coverage development at regular intervals in a one or more planted populations of *Glycine max* soybean germplasm for a period of time comprising a number of observed;
calculating an average canopy coverage (ACC) for each of the one or more planted populations of *Glycine max* soybean germplasm using equation (2):

$$ACC = \int_{t_0}^{t_n} f(cc_t)\partial(cc_t) = \frac{1}{N}\sum_{t_0}^{t_n} cc_t \quad (2)$$

wherein N is the number of observed days, cc is the canopy coverage for any point in time (t) within the time period for each population, $t_0$ is a first day of the time period, and $t_n$ is a last day of the time period;
comparing the calculated ACC of each of the one or more planted populations with a reference ACC, the reference ACC calculated using equation (2) and canopy coverage measurements taken over the period of time from a reference population of *Glycine max* soybean germplasm with a desired phenotype, wherein a calculated ACC from the one or more planted populations matching or being higher than the reference ACC is indicative of such population of *Glycine max* soybean germplasm exhibiting the desired phenotype;
selecting the one or more planted populations of *Glycine max* soybean germplasm as a breeder line where the calculated ACC of such population matches or is higher than the reference ACC;
planting and growing a progeny crop descendant from the selected breeder line that expresses the desired phenotype; and
wherein:
the desired phenotype is associated with at least one quantitative trait locus at soybean chromosome 19 and comprises canopy coverage at all days within the period of time; and
the period of time is 14 to 64 DAP and spans phenological stages V2 to R5 of the one or more planted populations of *Glycine max* soybean germplasm.

17. A method for selection of one or more breeder lines with a desired phenotype in *Glycine max* soybean plants, the method comprising:
measuring canopy coverage development at regular intervals in a one or more planted populations of *Glycine max* soybean germplasm for a period of time comprising a number of observed;
calculating an average canopy coverage (ACC) for each of the one or more planted populations of *Glycine max* soybean germplasm using equation (2):

$$ACC = \int_{t_0}^{t_n} f(cc_t)\partial(cc_t) = \frac{1}{N}\sum_{t_0}^{t_n} cc_t \quad (2)$$

wherein N is the number of observed days, cc is the canopy coverage for any point in time (t) within the time period for each population, $t_0$ is a first day of the time period, and $t_n$ is a last day of the time period;
comparing the calculated ACC of each of the one or more planted populations with a reference ACC, the reference ACC calculated using equation (2) and canopy coverage measurements taken over the period of time from a reference population of *Glycine max* soybean germplasm with a desired phenotype, wherein a calculated ACC from the one or more planted populations matching or being higher than the reference ACC is indicative of such population of *Glycine max* soybean germplasm exhibiting the desired phenotype;

selecting the one or more planted populations of *Glycine max* soybean germplasm as a breeder line where the calculated ACC of such population matches or is higher than the reference ACC; and planting and growing a progeny crop descendant from the selected breeder line that expresses the desired phenotype;

wherein the desired phenotype is higher biomass production as compared to a planted population of *Glycine max* soybean germplasm having a calculated ACC that is less than the reference ACC.

* * * * *